(12) United States Patent
Blick et al.

(10) Patent No.: US 9,329,126 B2
(45) Date of Patent: May 3, 2016

(54) MASS SPECTROMETER DETECTOR USING OPTICALLY ACTIVE MEMBRANE

(71) Applicants: Wisconsin Alumni Research Foundation, Madison, WI (US); University of Hamburg, Hamburg (DE); The University of Massachusetts, Boston, MA (US)

(72) Inventors: Robert H. Blick, Hamburg (DE); Jonathan Rodriguez, Sun Prairie, WI (US); Hyunseok Kim, Madison, WI (US); Zlatan Aksamija, Hadley, MA (US); Wolfgang Hansen, Hamburg (DE); Christian Heyn, Lueneburg (DE)

(73) Assignees: Wisconsin Alumni Research Foundation, Madison, WI (US); University of Hamburg, Hamburg (DE); The University of Massachusetts, Boston, MA (US)

( * ) Notice: Subject to any disclaimer, the term of this patent is extended or adjusted under 35 U.S.C. 154(b) by 0 days.

(21) Appl. No.: 14/467,722

(22) Filed: Aug. 25, 2014

(65) Prior Publication Data

US 2016/0054224 A1 Feb. 25, 2016

(51) Int. Cl.
*G01N 21/64* (2006.01)
*H01J 49/26* (2006.01)
*H01J 49/02* (2006.01)

(52) U.S. Cl.
CPC .............. *G01N 21/64* (2013.01); *H01J 49/025* (2013.01); *H01J 49/26* (2013.01)

(58) Field of Classification Search
CPC .................................. H01J 49/02; H01J 43/24
USPC ...................................... 250/361 C, 281–283
See application file for complete search history.

(56) References Cited

U.S. PATENT DOCUMENTS

| 8,274,059 | B2 | 9/2012 | Blick |
| 8,507,845 | B2 | 8/2013 | Blick et al. |
| 8,686,375 | B2 | 4/2014 | Blick et al. |
| 2007/0023621 | A1* | 2/2007 | Blick .................... B82Y 15/00 250/251 |
| 2012/0305760 | A1* | 12/2012 | Blick ................... H01J 43/246 250/282 |

OTHER PUBLICATIONS

Fernandez-Lima et al.; Photon emission from massive projectile impacts on solids; Author Manuscript; Published in final edited form as: Surf Interface Anal. Jan. 2011; 43(1-2): pp. 53-57: Texas.

* cited by examiner

*Primary Examiner* — David Porta
*Assistant Examiner* — Meenakshi Sahu
(74) *Attorney, Agent, or Firm* — Boyle Fredrickson, S.C.

(57) ABSTRACT

A detector suitable for mass spectroscopy uses a thin membrane that converts the kinetic energy of impinging molecules into corresponding photons, the latter detected with a suitable photosensor. The arrival of molecules at the membrane is detected by detection of the corresponding photons.

17 Claims, 3 Drawing Sheets

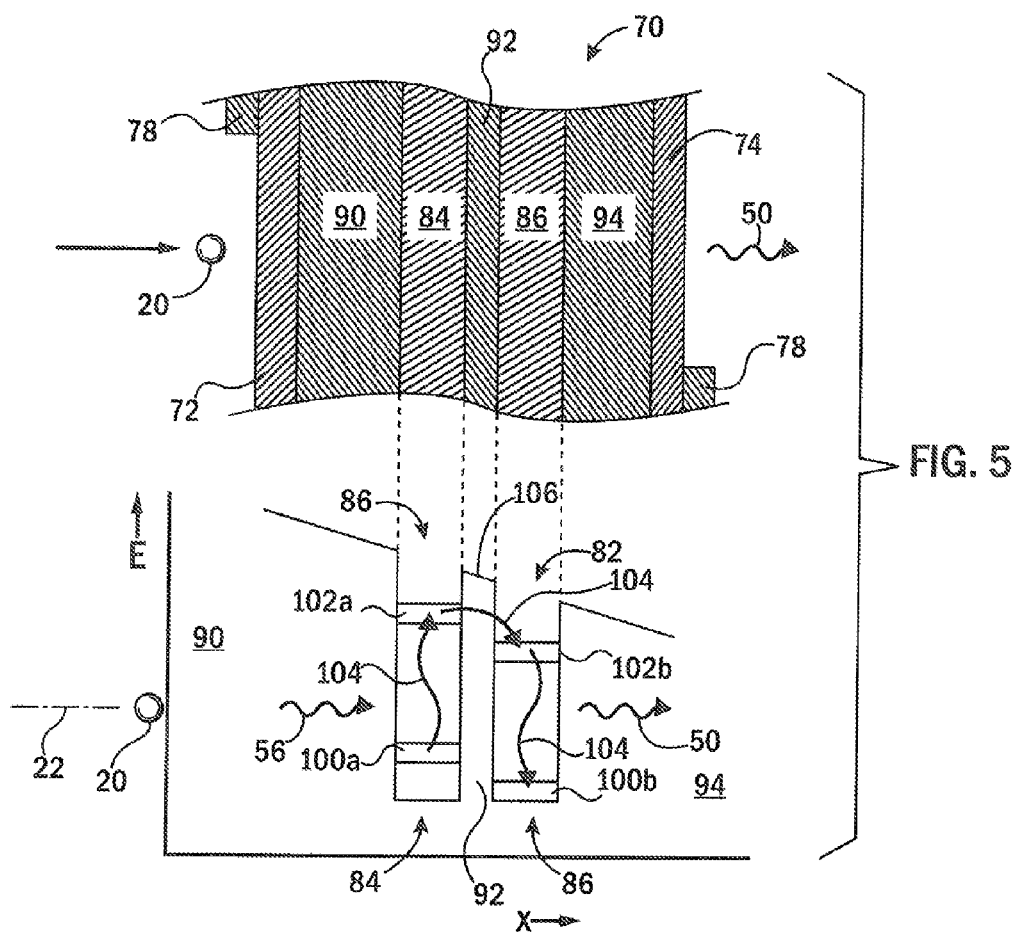
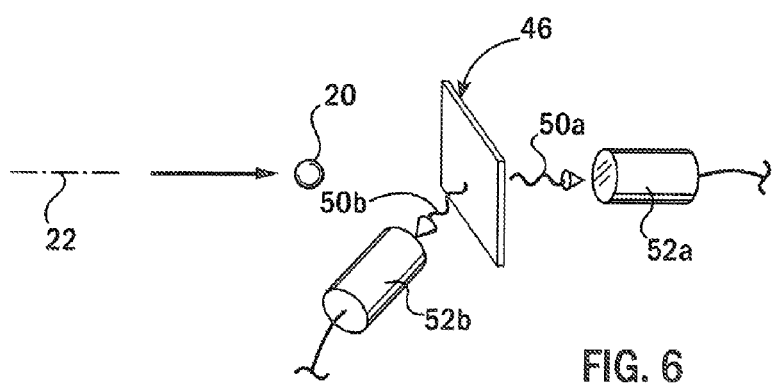

MASS SPECTROMETER DETECTOR USING OPTICALLY ACTIVE MEMBRANE

STATEMENT REGARDING FEDERALLY SPONSORED RESEARCH OR DEVELOPMENT

This invention was made with government support under FA9550-08-1-0337 awarded by the USAF/AFOSR. The government has certain rights in the invention.

CROSS REFERENCE TO RELATED APPLICATION

BACKGROUND OF THE INVENTION

The present invention relates to mass spectrometers and the like and in particular to a detector suited for, but not limited to, the detection of large ionized molecules in a mass spectrometer.

Mass spectrometers are analytic instruments that may provide for the precise measurement of the mass of molecules. Generally, the molecules to be measured are given an electrical charge and then accelerated by an electrical field. The velocity of their acceleration will be generally proportional to the mass-to-charge ratio (m/z) and so for a given and known charge the mass may be precisely determined by a charge, velocity, or energy measurement.

One method of determining velocity is the use of a "sector" type analyzer, which bends the trajectories of the charged particles using a magnetic field. When the particles exit the magnetic field, the angle of their trajectories (and spatial separation at a measurement point) will be in proportion to m/z and may be measured by a series of spatially separated collectors.

An alternative detection system uses a "time of flight" analyzer in which relative velocities of different molecular species are deduced based on the time it takes them to reach a detector. Common detectors used for time of flight analysis include so-called "Faraday cups" which are conductive metal cups, which catch charged particles and are attached to sensitive electrical amplifiers and "dynode" or microchannel detectors, which provide an amplification of received charge through electron multiplier techniques.

Mass spectrometry is increasingly applied to extremely large molecules, for example, proteins, that may be ionized by various techniques such as matrix assisted laser desorption/ionization (MALDI) in which the fragile proteins are protected with a matrix material that is struck by a laser beam. The matrix absorbs the energy of the beam and is removed from the protein while transferring a charge to the protein.

The large mass of proteins and similar bio-molecules decreases the sensitivity of a time of flight spectrometer because the velocity of the proteins is lower and thus the difference between velocities of large masses is less. In addition, common microchannel detectors experience a decrease in secondary electron yield with increasing ion mass.

U.S. Pat. Nos. 8,274,059; 8,507,845; and 8,686,375, all assigned to the same assignee as the present invention and hereby incorporated by reference, teach detector systems for large ions that provide detector membranes that convert the kinetic energy of the impinging ions, at a front surface of the membrane, into electrons ejected from the rear surface of the membrane by field emission and/or secondary electron emission. The ejected electrons may be then detected by a microchannel plate. By combining the membrane in front of the microchannel plate, improved sensitivity to large molecules may be obtained.

SUMMARY OF THE INVENTION

The present invention provides a detector that incorporates a thin membrane converting the kinetic energy of molecules impinging on its front surface into photons emitted through a rear and/or front surface. The photons are detected and converted to an electrical signal.

By using photons as a detection intermediary, it is believed that greater sensitivity to the detection of large molecules may be realized, in part, through greater signal-to-noise ratio of the detected signal. Photon intermediaries may further permit improved spatial discrimination with respect to the point of impingement of the molecule on the membrane, information that can be valuable for sector-type mass spectroscopy applications.

In one embodiment, the invention provides a detector that may detect impinging molecules. The detector includes a membrane positioned to receive impinging molecules at a front face and provides a structure converting the kinetic energy of the impinging molecules to light photons emitted from a rear or front face of the membrane. An electronic photosensor is positioned to detect photons from the membrane to provide an electric signal corresponding to receipt of impinging molecules.

It is thus a feature of at least one embodiment of the invention to provide light-mediated detection of the kinetic impact of large molecules, a detection mechanism that may be more sensitive to the impact of large molecules and/or which may provide better spatial sensitivity.

The membrane may be structured to provide room temperature light emission from at least a 5 kDa molecule impinging on the membrane with the kinetic energy of 25 keV.

It is thus a feature of at least one embodiment of the invention to provide a structure that may allow the detection of single large molecule impacts.

The membrane dimensions may be constrained to prevent kinetic energy of the impinging ionized molecules from being dissipated as heat without stimulation of electrons between quantum states.

It is thus a feature of at least one embodiment of the invention to promote photon emission over thermal energy dissipation by control of the membrane structure size.

The membrane may provide at least one quantum-well defining quantum states through which electrons may be promoted by the kinetic energy of the impinging molecule and in which electrons may decay to provide radiative relaxation emitting the photons.

It is thus a feature of at least one embodiment of the invention to promote photon emission stimulated by phonons through the use of a quantum-well structure.

The membrane may include a semiconducting material.

It is thus a feature of at least one embodiment of the invention to employ a material that can be fabricated using well-established integrated circuit techniques to produce thin membranes and/or heterostructures.

The membrane may provide an assembly of different materials producing at least one quantum-well, the quantum-well defining quantum states through which electrons may be promoted by the kinetic energy of the impinging molecule and through which electrons may decay to provide radiative relaxation emitting the photons.

It is thus a feature of at least one embodiment of the invention to provide a simple method of fabricating quantum-wells using different materials, for example, semiconductor materials of different bandgap levels.

The membrane may provide two quantum-wells proximate to each other to permitting tunneling therebetween.

It is thus a feature of at least one embodiment of the invention to provide a dual coupled quantum-well structure that may permit improved sensitivity.

The detector may employ electrical conductors adjacent respectively to the front and rear surface of the membrane to allow the imposition of an electrical field therebetween.

It is thus a feature of at least one embodiment of the invention to provide an energy offset between quantum states of the two adjacent quantum-wells to provide a method of supplying electron-hole pairs to the quantum-wells from an external energy source such as may promote sensitivity.

The photosensor may provide for multiple channels selectively receiving photons from different portions of the rear face to identify a location of photon emission caused by an impinging molecule over an area of the membrane.

It is thus a feature of at least one embodiment of the invention to provide a spatially discriminating detector that can determine a location on the membrane where the molecule strikes.

The photosensor may provide at least one electron multiplier.

It is thus a feature of at least one embodiment of the invention to employ an extremely sensitive light detector to enhance sensitivity of the device.

The impinging molecules may be ionized.

It is thus a feature of at least one embodiment of the invention to provide a detector suitable for use with ionized molecules in mass spectroscopy.

The detector may include an electronic computer executing a stored program and communicating with the detector to record the quantity of molecules striking the front face.

It is thus a feature of at least one embodiment of the invention to permit sensitive experiments in which molecule arrivals must be quantified. The invention contemplates that individual molecule strikes may be detected.

The detector may further include an assembly for receiving and ionizing molecules for analysis and at least a first and second electrode for accelerating ionized molecules received from the assembly along a path directed to the membrane. The electronic computer may execute the stored program to output a spectrograph.

It is thus a feature of at least one embodiment of the invention to provide an improved mass spectrograph suitable for measuring small quantities of large molecules.

These particular objects and advantages may apply to only some embodiments falling within the claims and thus do not define the scope of the invention.

BRIEF DESCRIPTION OF THE DRAWINGS

FIG. 5 is a simplified cross-sectional view of one embodiment of a membrane element providing for coupled quantum-wells, the cross-sectional view aligned with a quantum-well diagram showing the energy states of the quantum-wells; and FIG. 6 is a fragmentary diagram of the system of claim 1 configured to detect light from both a front and rear surface of the membrane array

DETAILED DESCRIPTION OF THE PREFERRED EMBODIMENT

Figure 1:
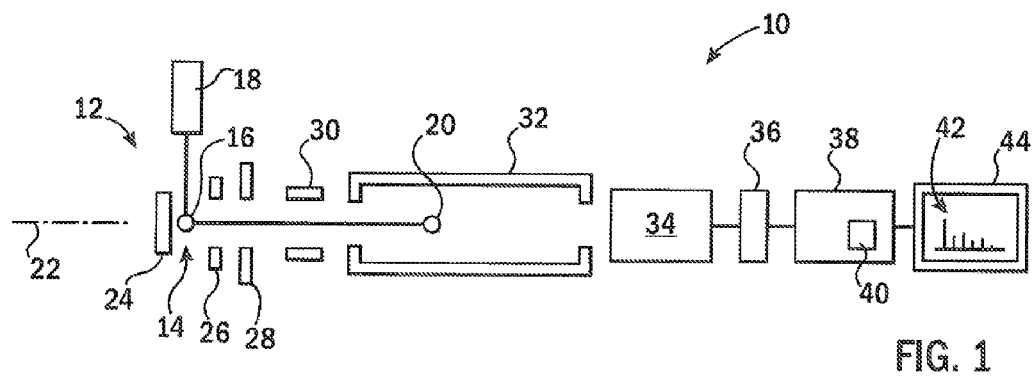
FIG. 1 is a simplified diagram of a matrix assisted laser desorption/ionization, time of flight (MALDI-TOF) mass spectrometer such as may be used with the detector of the present invention.

Referring now to FIG. 1, an example mass spectrometer 10 suitable for use with the present invention may include an ion generator 12, for example, providing an introduction zone 14 into which matrix treated molecules 16 may be introduced and targeted by a laser 18 to provide a source of ions 20. The ions 20 may be large molecules such as proteins, peptides, oligonucleotides and the like, that may be difficult to detect by conventional techniques.

The ions 20 may be accelerated along a travel axis 22 by means of various accelerating plates, for example, a repeller plate 24, positioned on a rear side of the introduction zone 14 and an attractor plate 26 positioned on the front side of the introduction zone 14 (in the direction of desired ion travel) with the attractor plate 26 having a relatively lower electrical potential than the repeller plate 24 (for positive ions). An accelerator plate 28 behind the attractor plate 26 may further accelerate the ions 20 to a desired speed. The ions 20 may be focused by a set of steering plates 30 as understood in the art to enter a flight tube 32 providing a zone when the ions 20 of different velocities may further separate, improving the resolution of the system. The ions may then enter a detector 34.

The detector may provide electrical signals to processing electronics 36 including, for example, amplifiers, filters and other signal processing elements understood to those of ordinary skill in the art. Output from the processing electronics 36 may be provided to an electronic computer 38 having a stored program 40 that may process the received electrical signals to provide a spectrograph output 42, for example, on a display monitor 44 providing information about the mass of the ions 20. Generally the electronic computer 38 will include a fast (bandwidth ~500-MHz) data acquisition board which allows the electronic computer 38 to operate manner of a high speed oscilloscope.

Figure 2:
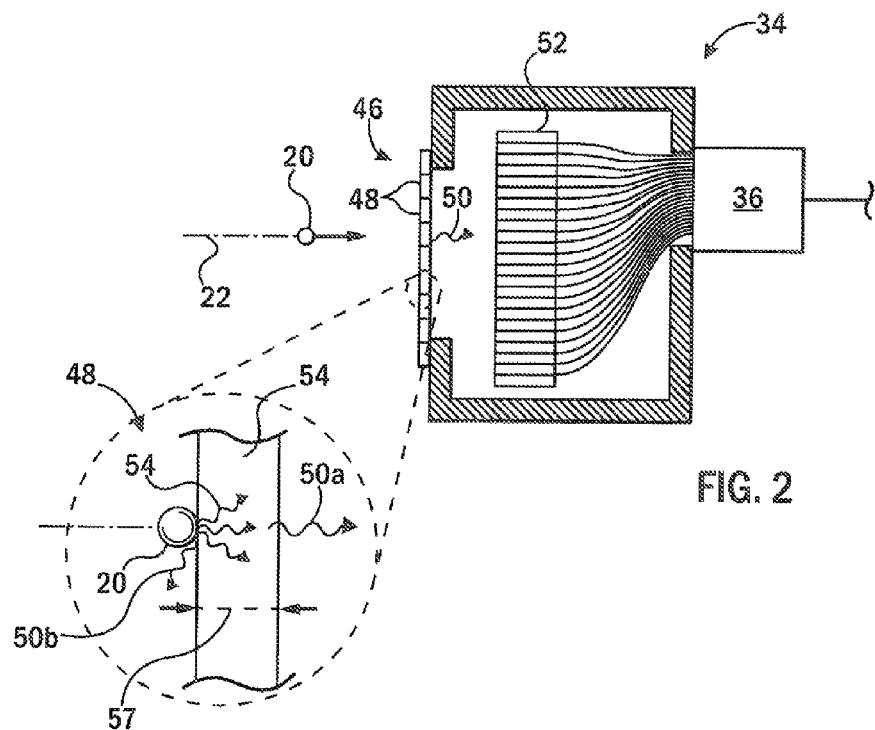
FIG. 2 is a simplified enlarged cross-section of the detector of FIG. 1 having a membrane array positioned in front of a photodetector array, and further showing in an inset, a cross-sectional detail of one membrane array element.

Referring now to FIG. 2, the detector 34 of the present invention provides a membrane array 46 extending in a plane generally perpendicular to the axis 22. The membrane array 46 includes multiple array elements 48 arranged in rows and columns, each of which may receive one or more impinging ions 20 accelerated against a front surface of the array element 48. As will be discussed in greater detail below, the kinetic energy of the impinging ions 20 generates corresponding output photons 50a radiating from a rear surface of the array element 48 to be received by a photodetector 52. As will be discussed below, additional output photons 50b may radiate from a front surface of the array element 48.

In one embodiment, the photodetector 52 may be a multi-channel light amplifier such as a photomultiplier array (such as when using avalanche photodiodes) able to detect and spatially locate photons 50 from one or more ions 20 over its area. In this way the detector 34 may distinguish in time and/or space closely adjacent impacts by impinging ions 20.

Signals from the photodetector 52 are output from the detector 34 to the processing electronics 36 described above.

Referring still to FIG. 2, each array element 48 provides a thin membrane 54 supported only at its periphery and sized so that the kinetic, which is transferred into acoustic energy (phonons) 56 of the impinging ion 20 is constrained so that it is not dissipated (laterally) as heat before the stimulation of the membrane material necessary to produce the photon 50. In one embodiment, the membrane 54 has a thickness 57 between five nanometers and 15 micrometers. In another embodiment the membrane 54 has a thickness between 20 nanometers and 50 nanometers.

The constraint dimensions of the membrane 54 ensure that light photons 50 are generated substantially only by radiative decay of electrons between quantized states and not by more conventional thermal emission. In this regard it is expected that the acoustic energy 56 will be transferred by high-energy ballistic phonons. As will be discussed below, the membrane 54 may be constructed of one or more semiconductor materials stacked together and providing interfaces perpendicular to the axis 22.

Figure 3:
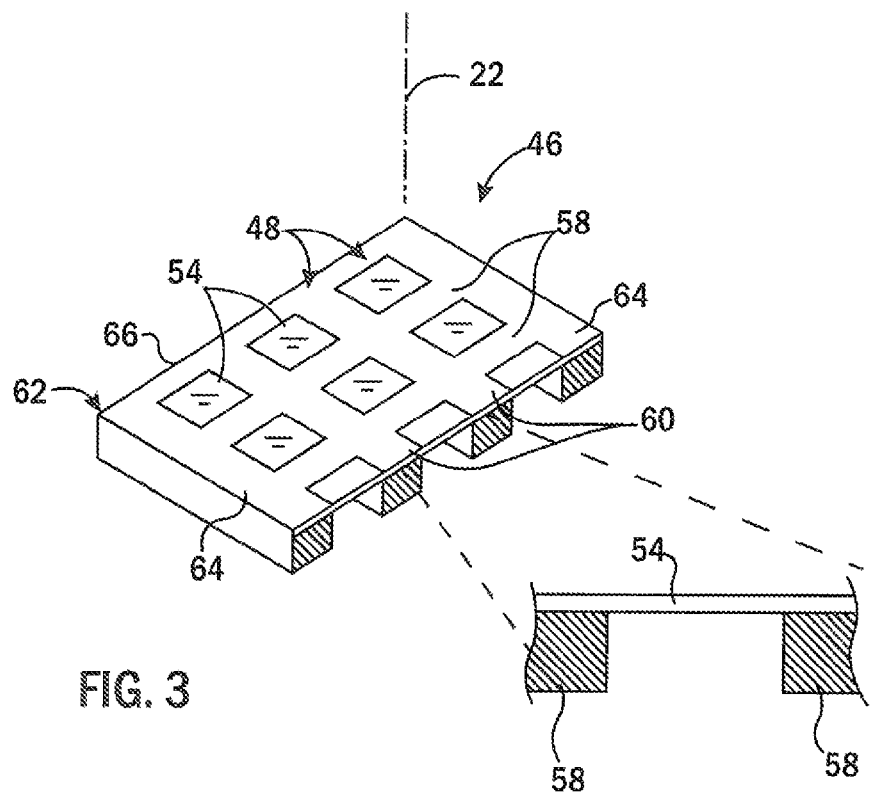
FIG. 3 is a perspective, fragmentary view of the membrane array of FIG. 2 with an expanded cross-sectional view of a membrane and its supporting array structure for one membrane element.

Referring now to FIG. 3, the membranes 54 of each array element 48 may be supported in the membrane array 46 by crossing supporting mullions 58 and muntins 60 providing a rectangular frame around each membrane 54. The mullions 58 and muntins 60 are in turn supported within an outer peripheral frame 62 comprised of upper and lower rails 64 and left and right stiles 66. The extremely thin membrane 54 may thus be adequately supported around its entire periphery by a thicker surrounding structure and may be fabricated by selectively etching from a larger structure. For example, photochemical etching of a substrate material to expose the membrane 54 and preserve the mullions 58, muntins 60, and outer frame 62, may be performed. The fabrication process may be generally analogous to that described in U.S. Pat. No. 8,274,059 cited above and may make use of photolithographic manufacturing processes known in the art.

For example, the supporting structure of the mullions 58 and muntins 60 and outer peripheral frame 62 may be a silicon substrate of a silicon-on-insulator (SOI) wafer having a layer of silicon dioxide separating the silicon substrate structure from an upper silicon layer on which the membrane 54 is fabricated, for example, by physical or chemical vapor deposition or other similar techniques.

Figure 4:
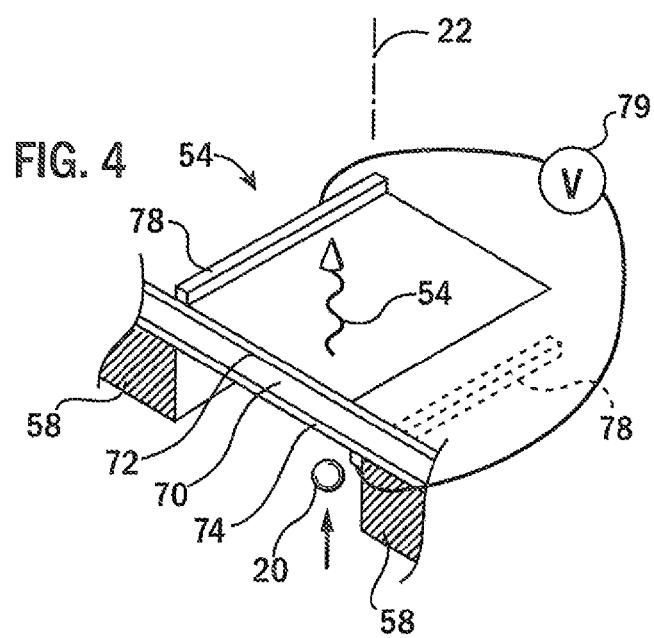
FIG. 4 is a perspective fragmentary view of the membrane element of FIG. 3 showing attachment points for biasing voltage.

Referring now to FIGS. 4 and 5, in one embodiment, the membrane 54 may comprise multiple stacked internal layers 70 extending generally perpendicular to axis 22. The multiple stacked internal layers 70 may be clad with a front conductive layer 72 receiving the ions 20 and a rear conductive layer 74 through which the photons 50 are emitted. The front conductive layer 72 and rear conductive layer 74, for example, may be each a light-transmissive, five nanometer thick layer of Si or GaAs doped to a conductive state as is understood in the art and attached to respective metallization electrodes 78. The metallization electrodes 78 may be displaced along opposed edges of the membrane 54 so as not to obstruct exiting light photons 50 at the rear face or impinging ions 20 at the front face. The electrodes 78 may be attached to an electrical DC voltage source 79 also connected in parallel to all other membranes 54 and imposing an electric field along axis 22 through the membrane 54 as will be described below.

In one embodiment, the multiple stacked internal layers 70 provide quantum heterostructures creating two adjacent quantum-wells 80 and 82 caused by the confinement of charge carriers in thin well layers 84 and 86 by dissimilar barrier layers 90, 92 and 94. Specifically, a frontmost barrier layer 90 may fit against a front face of a first well layer 84, and a barrier layer 92 may be positioned between well layers 84 and 86, and barrier layer 94 may fit against a rear face of well layer 86.

It will be appreciated that the structure of FIG. 4 may also be used in a fashion inverted from what is shown when accompanied by a simple reversal of the polarity of the voltage from source 79. In this case, the ions 20 will be received downward on the upper surface of the membrane as depicted.

In one embodiment the well layers 84 and 86 may be eight nanometer thick layers of group III/V semiconductors, for example, gallium arsenide (GaAs), while barrier layer 92 may be a five nanometer layer of aluminum gallium arsenide (AlGaAs), and barrier layers 90 and 94 may be each thirty nanometer thick layers of AlGaAs. The AlGaAs of barrier layers 90, 92 and 94 will have similar lattice constants to GaAs of well layers 84 and 86 but a substantially larger bandgap thereby constraining charge carriers against moving through the boundary by misalignment of the energy bands.

The barrier layer 90, 92 and 94 constrain the movement of charge carriers in the well layers 84 and 86 to a small dimension that generates in each of the well layers 84 and 86 a quantum-well enforcing a set of discrete energy levels or bands 100 and 102 within the quantum-well layers 84 and 86 with a sharp density of states characteristic of quantum-wells.

The electrical biasing provided by the voltage source 79 of FIG. 4 elevates the energy bands 100*a* and 102*a* of well layer 84 with respect to the energy bands 100*b* and 102*b* of well layer 86. By adjusting the electrical voltage, the two quantum-wells 80 and 82 may be tuned to provide a resonant electronic transition between quantum-well 80 and quantum-well 82.

While the inventors do not wish to be bound by a particular theory, the resulting structure is believed to be capable of receiving the acoustic energy 56 from a striking ion 20, passing through conductive layer 72 and barrier layer 90, to cause an excitation of electrons 104 in the quantum-well 80 formed by well layer 84 from energy band 100*a* to energy band 102*a*. Energy tunneling 106 of the electrons 104 through barrier layer 92 into well layer 86 may then occur, and then the electrons 104 may spontaneously decay from energy band 102*b* to energy band 100*b* causing a radiative emission of photons 50, the latter passing through barrier layer 94 and conductive layer 74.

The double quantum-well structure is believed to provide increased sensitivity but may alternatively be replaced with a single layer structure omitting barrier layer 92 and well layer 86. Generally the amount of energy required to modify photon emissions should be much lower than that needed to generate field-emissions of the prior art. It is expected that the membrane may provide room temperature light emission from a 5 kDa to 5 MDa molecule impinging on the membrane with the kinetic energy of 25 keV.

Electrical voltage of voltage source 79 provides an independent source of charge carriers increasing the sensitivity of the system. An alternative approach may use optical carrier injection from a laser or the like. The electrical voltage may also be used to tune the detector sensitivity.

Referring now to FIG. 6, the membrane array 46, upon receipt of ion 20 may emit light both from a rear surface (photon 50*a*) as has been discussed to be received by photodetector 52*a*. In addition, the membrane array 46 may emit light from the front surface (photon 50*b*) which may be detected also or alternatively by a corresponding photodetector 52*b* positioned out of the line of travel of the ion 20. In this case, signals from both the photodetectors 52*a* and 52*b* may be received by the computer 38 for independent or joint processing.

The present invention is not limited to a mass spectrometer of the MALDI-TOF design as described in simplified form above but may be used in any time-of-flight mass spectrometers including those that provide for reflection of the ions and other features well known in the art. Although the present detector is particularly desirable for large molecules such as proteins where high temporal resolution is required, it may find use in general-purpose spectroscopy as well.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference, which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a microprocessor" and "a processor" or "the microprocessor" and "the processor," can be understood to include one or more microprocessors that can communicate in a stand-alone and/or a distributed environment(s), and can thus be configured to communicate via wired or wireless communications with other processors, where such one or more processors can be configured to operate on one or more processor-controlled devices that can be similar or different devices. Furthermore, references to memory, unless otherwise specified, can include one or more processor-readable and accessible memory elements and/or components that can be internal to the processor-controlled device or external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

We claim:

1. A detector for use in detecting impinging molecules comprising:
   a membrane positionable to receive impinging molecules at a front face, the membrane adapted to convert a kinetic energy of at least one impinging molecule to at least one light photon emitted from the membrane; and
   an electronic photosensor positioned to detect light photons from membrane caused by at least one molecule impinging on the front face of the membrane to provide an electric signal corresponding to receipt of at least one molecule impinging on the front face of the membrane;
   wherein the light photons are generated substantially only by a radiative decay of electrons between quantized energy states; and
   wherein the membrane provides at least one quantum-well formed of a series of membrane layers and defining quantum states through which electrons may be promoted by the kinetic energy of the impinging molecule and through which electrons may decay to provide radiative relaxation emitting the photons.

2. The detector of claim 1 wherein the membrane is adapted to provide room temperature light emission from at least a 5 kDa molecule impinging on the membrane with the kinetic energy of 25 keV.

3. The detector of claim 1 wherein the membrane dimensions are constrained to prevent kinetic energy of the impinging ionized molecules from being dissipated as heat laterally without stimulation of electrons between quantum states.

4. The detector of claim 3 wherein the membrane has a thickness between five nanometers and 15 micrometers.

5. The detector of claim 4 wherein the membrane has a thickness between 20 and 500 nanometers.

6. The detector of claim 1 wherein the membrane includes a semiconducting material.

7. The detector of claim 1 wherein the membrane provides an assembly of different materials producing at least one quantum-well defining quantum states through which electrons may be promoted by the kinetic energy of the impinging molecule and through which electrons may decay to provide radiative relaxation emitting the photons.

8. The detector of claim 7 wherein the different materials are different semiconductors.

9. The detector of claim 1 wherein the membrane provides two quantum-wells adjacent to permit tunneling therebetween.

10. The detector of claim 9 further including electrical conductors adjacent respectively to the front and rear surface of the membrane to provide an electrical field therebetween to provide an energy offset between quantum states of the two adjacent quantum-wells.

11. The detector of claim 1 wherein the electronic photosensor provides for multiple channels selectively receiving photons from different portions of the rear face to identify a location of photon emission caused by an impinging molecule over an area of the membrane.

12. The detector of claim 1 wherein the electronic photosensor provides at least one electron multiplier.

13. The detector of claim 1 wherein the impinging molecules are ionized.

14. The detector of claim 1 further including an electronic computer executing a stored program and communicating with the detector to record the quantity of molecules striking the front face.

15. The detector of claim 14 further including:
   an assembly for receiving and ionizing molecules for analysis;
   at least a first and second electrode for accelerating ionized molecules received from the assembly along a path directed to the membrane; and
   wherein the electronic computer executes the stored program to output a spectrograph.

16. A method of characterizing molecular weights comprising the steps of:
 (a) providing a source of ionized molecules for analysis;
 (b) accelerating the ionized molecules in an electric field toward a membrane positioned to receive impinging molecules at a front face, the membrane adapted to convert a kinetic energy of at least one impinging molecule to at least one light photon emitted from a rear face of the membrane; and
 (c) detecting at least one light photon at an electronic photosensor positioned to detect light photons from the membrane caused by at least one molecule impinging on the front face of the membrane to provide an electric signal indicating a receipt of at least one molecule; and
 (d) analyzing the electric signal with detection electronics to detect arrival of the ionized molecules at the membrane;
 wherein the light photons are generated substantially only by a radiative decay of electrons between quantized energy states; and
 wherein the membrane provides at least one quantum-well formed of a series of membrane layers and defining quantum states through which electrons may be promoted by the kinetic energy of the impinging molecule and through which electrons may decay to provide radiative relaxation emitting the photons.

17. The method of claim 16 wherein step (d) further analyzes the arrival of the ionized molecules at the membrane according to a method selected from the group consisting of measuring a time of arrival of the molecules at the front surface of the membrane and measuring a spatial location of the arrival of the molecules on the front surface of the membrane.

* * * * *